(12) United States Patent
Lee et al.

(10) Patent No.: US 8,476,600 B2
(45) Date of Patent: Jul. 2, 2013

(54) APPARATUS AND METHOD FOR MEASURING DEPTH-OF-INTERACTION USING LIGHT DISPERSION AND POSITRON EMISSION TOMOGRAPHY USING THE SAME

(75) Inventors: Jae Sung Lee, Seoul (KR); Mikiko Ito, Seoul (KR); Seong Jong Hong, Seoul (KR)

(73) Assignee: Snu R&DB Foundation, Seoul (KR)

( * ) Notice: Subject to any disclaimer, the term of this patent is extended or adjusted under 35 U.S.C. 154(b) by 649 days.

(21) Appl. No.: 12/766,638

(22) Filed: Apr. 23, 2010

(65) Prior Publication Data

US 2010/0270463 A1  Oct. 28, 2010

(30) Foreign Application Priority Data

Apr. 24, 2009 (KR) ........................ 10-2009-0035826

(51) Int. Cl.
*G01T 1/20* (2006.01)
(52) U.S. Cl.
USPC .................................................... 250/370.11
(58) Field of Classification Search
USPC .................................................... 250/370.11
See application file for complete search history.

(56) References Cited

U.S. PATENT DOCUMENTS

| 5,329,124 | A | * | 7/1994 | Yamamoto et al. | 250/367 |
| 5,576,546 | A | * | 11/1996 | Gagnon | 250/369 |
| 5,760,401 | A | * | 6/1998 | Nelleman et al. | 250/363.03 |
| 7,932,497 | B2 | * | 4/2011 | Laurence et al. | 250/363.04 |
| 2009/0008562 | A1 | | 1/2009 | Grazioso et al. | 250/363.04 |
| 2009/0032717 | A1 | | 2/2009 | Aykac et al. | 250/367 |
| 2009/0224164 | A1 | * | 9/2009 | Lewellen et al. | 250/370.11 |

FOREIGN PATENT DOCUMENTS

JP  2009-53104  3/2009

OTHER PUBLICATIONS

Lee et al., "A novel method to determine the depth of interaction position in the pixilated scintillation crystals with singe-ended readout by multi-anode PMT", The Journal of Nuclear Medicine, 2009, pp. 1-23.

* cited by examiner

*Primary Examiner* — David Porta
*Assistant Examiner* — Edwin Gunberg
(74) *Attorney, Agent, or Firm* — Allen, Dyer, Doppelt, Milbrath & Gilchrist, P.A.

(57) ABSTRACT

The present invention provides an apparatus for measuring a Depth-Of-Interaction (DOI), comprising a crystal layer 10 of a mono layer in which a plurality of crystals for absorbing gamma rays are consecutively arranged, scintillation light detectors disposed at one end of the crystals and configured to detect scintillation light emitted from the crystal layer 10 by the gamma rays, change means included in the crystals and configured to linearly change transmittance in a length direction of the crystals, and a control unit 30 configured to calculate the DOI in the crystal layer 10 on a basis of the first output signal and the second output signal. The scintillation light detector outputs the first output signal in one direction and the second output signal in a direction at a right angle to the one direction.

21 Claims, 14 Drawing Sheets

111

APPARATUS AND METHOD FOR MEASURING DEPTH-OF-INTERACTION USING LIGHT DISPERSION AND POSITRON EMISSION TOMOGRAPHY USING THE SAME

BACKGROUND OF THE INVENTION

1. Field of the Invention

The present invention relates to an apparatus and method for measuring a Depth-Of-Interaction (hereinafter referred to as a 'DOI') which is capable of improving the spatial resolution in a Positron Emission Tomography (hereinafter referred to as a 'PET'). More particularly, the present invention relates to an apparatus and method for measuring a DOI using a light dispersion property within the crystal layer of a mono layer into which reflective films are inserted, and a PET using the same.

2. Background of the Related Art

The PET (Positron Emission Tomography) is a tomography using radioactive rays, such as X-ray Computerized Tomography (CT) tomography and a Single Photon Emission Computerized Tomography (SPECT).

The PET is typically a technique for imaging a distribution of foreign substances within the body by injecting a radioactive sample, emitting positrons, into an organism through an intravenous injection or inhalation and detecting the emitted positrons in order to conduct researches and diagnosis. This technique is the same principle as, for example, a technique of using FDG in which a radioactive isotope F-18 having a half life of about 110 minutes is combined with glucose in order to track cancer cells based on the fact that some cancer cells accumulate more glucose than other cells.

As described above, the PET is being used in metabolism researches on the human body, a diagnosis of cancer, and the diagnosis and researches for several diseases, such as the heart and nervous system abnormalities. A positron emission nuclide is an unstable isotope having some number of neutrons in a nucleus. Nuclides, such as O15, N13, C11, and F18, are mainly used in the PET.

Positrons emitted from the positron emission nuclides within the human body are combined with nearby electrons by a phenomenon called "pair annihilation," thus emitting γ-rays.

In accordance with the principle of the conservation of energy and law of conservation of momentum related to the mass-energy equivalence principal, the positrons being in a static state are combined with nearby electrons and then converted into annihilation gamma rays of 511-keV energy, which are emitted in the opposite directions. A position where γ-rays are generated can be determined by detecting and analyzing a pair of γ-rays emitted in the opposite direction. Accordingly, the occurrence frequency of γ-rays, that is, the accumulated concentration of a marked sample can be found as a function of spatial position coordinates. A distribution of radioactive nuclides within the body of an examinee can be known by displaying the results using display means, etc.

The most important factors to determine the performance of the PET are the spatial resolution and detection efficiency. To achieve improved performance, a method of densely arranging detectors having a smaller size is possible. This method is, however, disadvantageous in that a reduction in the size of components is limited and the cost is increased because of an increase in the number of detectors and electronic measuring instruments.

As a method of improving the spatial resolution, there is a method using DOI information. The term 'DOI' refers to a depth from a crystal to a place where scintillation light is generated. If the DOI information is unknown, a PET apparatus will have a significant error in determining a position where gamma rays has been generated because of the parallax errors in the peripheral field of view, inevitably resulting in a degraded spatial resolution. Accordingly, to maintain a certain spatial resolution and detection efficiency without causing deterioration in spatial resolution uniformity, DOI information within the crystal is used.

One of the DOI estimation methods is a method based on that the temporal characteristic or size of a scintillation light signal emission differs in multiple crystal layers with different properties. In this method, multiple crystal layers are formed in a DOI measurement apparatus in order to measure the DOI. However, this method is disadvantageous in that it provides only discrete DOI information, which is limited by the number of layers. Light losses between the layers and expense versus mono-layer crystal designs are also drawbacks of this method.

Another method of the DOI estimation is to count the number of photons using photosensors attached to both ends of a scintillation light crystal in the length direction. In this method, the DOI is measured as a ratio of detections because a photosensor close to a DOI position detects a greater number of scintillation light signals. This method is, however, disadvantageous in that a lot of costs are required because the photosensors have to be provided on both sides of the scintillation light crystal.

To solve the problem, there was a proposed method of measuring light shared between crystals by installing the photosensor only on one face of the scintillation light crystal in the length direction and combining a reflective film on a surface of the crystal. This method is based on that the reflective film is partially inserted between the crystals and the amount of light shared between the crystals is changed according to the depth of the crystal.

In particular, in the method, a pair of two scintillation light crystals is used as one scintillation light detector unit, light is shared only between the pair of two scintillation light crystals, and the number of photons shared only between the two scintillation light crystals is compared. Accordingly, if it is sought to measure light using a photomultiplier tube (hereinafter referred to as a 'PMT) of a multi-channel, it is indispensable to match the scintillation light crystal to each light pixel. If it is sought to measure light using photosensors, the photosensor must be attached to each crystal. This method is also problematic in that a DOI response is deteriorated because light is dispersed in all directions by glass between the light pixel and a surface of the PMT, and the manufacturing costs are increased because of an increase in the number of photosensors and of an increased size of electronic equipment accordingly. Accordingly, there has been a need for a model of a DOI measurement apparatus and a DOI measurement method using the same, which can solve the above-described problems.

SUMMARY OF THE INVENTION

Accordingly, the present invention has been made in view of the above problems occurring in the prior art, and it is an object of the present invention to provide an apparatus and method for measuring a DOI and a PET using the same, which are capable of improving the spatial resolution while using a crystal layer of a mono layer having a scintillation light detector provided only on one face of a crystal, in the case in which DOI information is acquired in order to improve the spatial resolution of PET equipment.

Another object of the present invention is to provide an apparatus and method for measuring a DOI and a PET using the same, which are capable of providing continuous DOI information by solving the discontinuity of DOI information in the existing model using multiple crystal layers.

Yet another object of the present invention is to provide an apparatus and method for measuring a DOI and a PET using the same, which are capable of solving the cost problems resulting from the provision of the photosensors on both sides of a crystal or the provision of the multi-layered crystal layers in the existing model.

The objects of the present invention can be achieved by an apparatus for measuring a Depth-Of-Interaction (DOI), comprising: a crystal layer 10 of a mono layer in which a multiple of crystals for absorbing gamma rays are adjacent and consecutively arranged, scintillation light detectors disposed at one end of the crystals and configured to detect scintillation light emitted from the crystal layer 10 by the gamma rays, change means included in the crystals and configured to linearly change transmittance in the length direction of the crystals, and a control unit 30 configured to calculate the DOI in the crystal layer 10 on the basis of a first output signal and a second output signal. The scintillation light detector outputs the first output signal in one direction and the second output signal in a direction perpendicular to the one direction.

The change means preferably is based on a coating concentration of reflective materials in the length direction of the crystals. Furthermore, the reflective materials preferably include white or silver paint.

Furthermore, the change means preferably comprises a reflective film inserted between the crystals. Furthermore, the reflective film preferably is based on a geometrical change of the reflective film in the length direction of the crystals.

Furthermore, the reflective film preferably is a triangular tooth film 111 having a long strip and a triangular shape in which a width of the crystal is a base and half a length of the crystal is a height on one face of the length direction, wherein the triangular shapes are repeatedly formed every width of the crystal.

Furthermore, the crystal preferably is a rectangular parallelepiped crystal 110 having a square cross-section. The triangular tooth films 111 preferably are consecutively arranged in parallel to one sides of the rectangular parallelepiped crystals 110 and inserted into the rectangular parallelepiped crystals 110 in a reverse phase on sides vertical to the one sides.

Furthermore, the rectangular parallelepiped crystal 110 preferably has a refractive index of 1.82 on an unpolished surface.

Furthermore, the crystal layer 10 preferably has a square in which an arrangement of the rectangular parallelepiped crystals 110 is 29 rows×29 columns.

Furthermore, the rectangular parallelepiped crystal 110 preferably has a square cross-section having one face of 1.5 mm and having a length of 12 mm to 24 mm.

Furthermore, the reflective film preferably is a film of a strip shape in which identical shapes are repeated for every width of one side of the crystal in one face of the length direction and is a diamond-shaped film 121 having a single form of a diamond shape or a triangular film 122 having a single form of a triangular shape.

The crystal preferably is a triangle pole-shaped crystal 120 having a regular triangle section. The diamond-shaped films 121 preferably are consecutively arranged in parallel to one side of the triangle pole-shaped crystals 120. The triangular films 122 preferably are consecutively arranged in parallel on the other side of the triangle pole-shaped crystals 120 crossing the one face. Inverse triangular films 123 preferably are consecutively arranged in a reverse phase of the triangular film 122 on remaining sides of the triangle pole-shaped crystals 120.

Furthermore, the reflective film preferably is based on a change in the concentration of the reflective film in the length direction of the crystals.

The reflective film preferably is a gradient film 112 having a rectangular strip of a rectangular shape, a coupling groove 130 formed for every width on one sides of the crystals, and a linear change in the concentration in the length direction of the crystals. Furthermore, the gradient film 112 preferably is formed by coating white or silver paint on transparent vinyl.

The crystal preferably is a rectangular parallelepiped crystal 110 having a square face. The gradient films 112 preferably are consecutively inserted into and arranged on the rectangular parallelepiped crystals 110 in parallel to one sides of the rectangular parallelepiped crystals 110 so that a top surface of the gradient films 112 becomes a transparent portion and are consecutively inserted into and arranged on the rectangular parallelepiped crystals 110 in a reverse phase of the gradient film 112 on the other side of the rectangular parallelepiped crystals 110, vertical to the one face, so that the gradient films 112 can be coupled with the coupling grooves 130.

Meanwhile, the crystal preferably is any one of LSO, BGO, and NaI crystals. Furthermore, the scintillation light detector preferably comprises a position-sensitive PMT 20 equipped with one or more light-sensitive pixels 200.

Furthermore, the position-sensitive Photo Multiplier Tube (PMT) 20 preferably has a structure in which the light-sensitive pixels 200 coupled with the crystal layer 10 are arranged to have a square structure of 16 rows×16 columns or 8 rows×8 columns.

The objects of the present invention can be achieved by a Positron Emission Tomography (PET) using light dispersion, using the DOI measurement apparatus.

The objects of the present invention can be achieved by a method of measuring a DOI using light dispersion, comprising: a step (S100) of scintillation light emitted from specific positions of a plurality of crystals which has absorbed gamma rays; a step (S200) of the crystals or reflective films, having a linearly changing transmittance in a length direction of the crystals, controlling a degree of dispersion of scintillation light; a step (S300) of scintillation light detectors 400, disposed on one end of the crystals, detecting the scintillation light; a step (S400) of the scintillation light detectors each detecting first output signal according to one direction corresponding to the scintillation light and a second output signal according to a direction at a right angle to the one direction; and a step (S500) of a control unit 30 calculating the DOI of the crystal on a basis of the first output signal and the second output signal.

Furthermore, the step (S500) of a control unit 30 calculating the DOI of the crystal on a basis of the first output signal and the second output signal preferably comprises a step (S510) of calculating an amount of a variance value of the number of photons in each of the directions on the basis of the first output signal and the second output signal; a step (S520) of inducing an angle of the DOI on the basis of the variance value of the number of photons; and a step 5530 of calculating the DOI on the basis of the angle of the DOI.

Furthermore, the DOI angle preferably is calculated using the following equation:

$$\theta_{doi} = \tan^{-1}\left(\frac{55 - \sigma_y^2}{55 - \sigma_x^2}\right)$$

where $\theta_{doi}$ is an angle of the DOI, $\sigma_x^2$ is a variance value in an x axis, and $\sigma_y^2$ is a variance value in an y axis.

BRIEF DESCRIPTION OF THE DRAWINGS

Further objects and advantages of the invention can be more fully understood from the following detailed description taken in conjunction with the accompanying drawings in which.

DESCRIPTION OF REFERENCE NUMERALS OF PRINCIPAL ELEMENTS IN THE DRAWINGS

Figure 1:
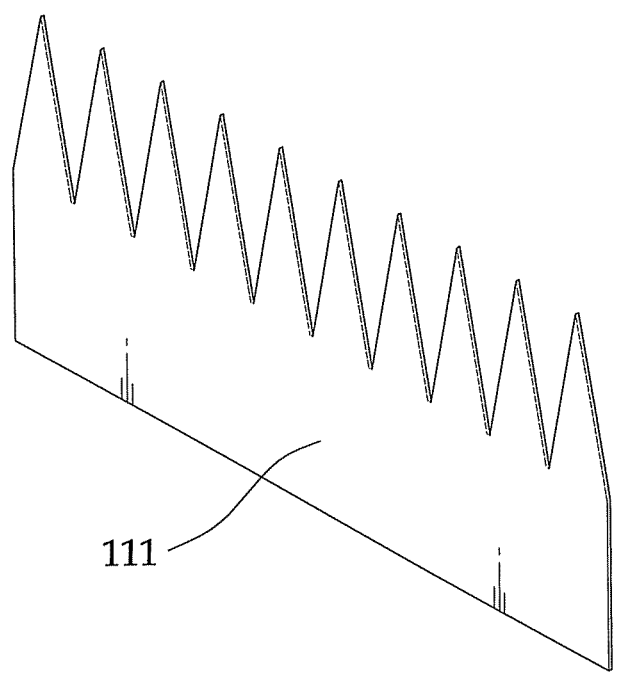
FIG. 1 is a perspective view of a reflective film according to a first embodiment of the present invention.

119: crystal layer 122: triangular film
110: rectangular parallelepiped crystal 130: coupling groove
120: triangle pole-shaped crystals 112: gradient film
111: triangular tooth film 20: position-sensitive PMT
121: diamond-shaped film 200: light-sensitive pixel
123: the inverse triangular film 30: control unit

DETAILED DESCRIPTION OF EMBODIMENTS

Some exemplary embodiments of the present invention will now be described in detail with reference to the accompanying drawings.

<First Embodiment>

FIG. 1 is a perspective view of a triangular tooth film 111 (i.e., a reflective film) according to a first embodiment of the present invention. The triangular tooth film has a strip shape having triangular shapes repeatedly formed on one side.

The triangular tooth film 111 has the triangular shape in which the width of crystals attached thereto is the base and half the length of the crystals is the height. In the present embodiment, the triangular tooth film 111 has a thickness of 0.065 mm, and it is made of ESR polymer materials having the reflectivity of 98%.

Figure 2:
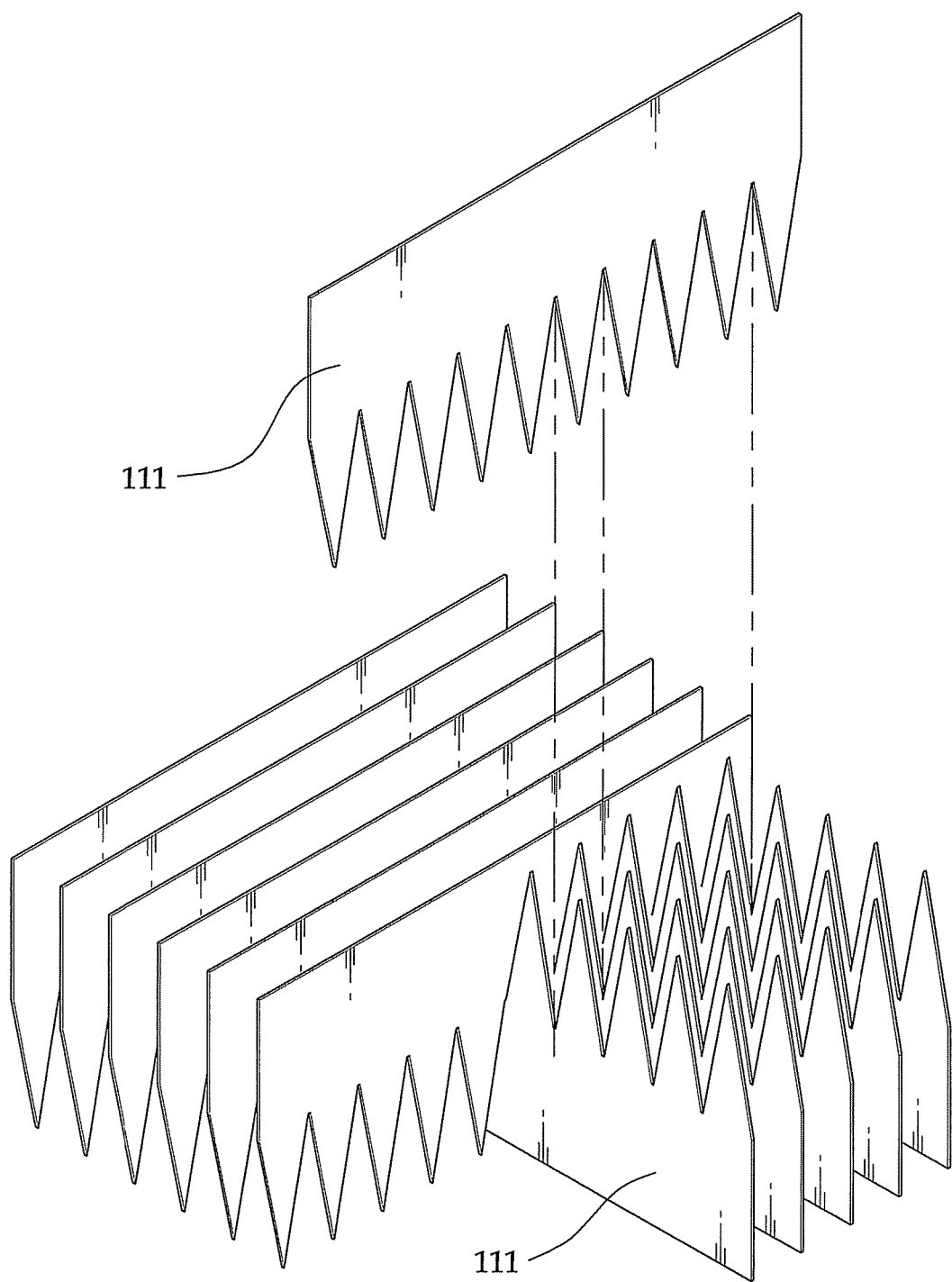
FIG. 2 is a perspective view of an assembly in which the reflective films shown in FIG. 1 are coupled together.

FIG. 2 is a perspective view of an assembly in which the triangular tooth films 111 shown in FIG. 1 are coupled together. A lattice structure is formed in which the triangular tooth films 111 are consecutively arranged in parallel to the one side of rectangular parallelepiped crystals 110 to which the triangular tooth films 111 are attached and the triangular tooth films 111 are consecutively inserted and arranged on one side at a right angle to the one side of the rectangular parallelepiped crystals 110 in a reverse phase.

Figure 3:
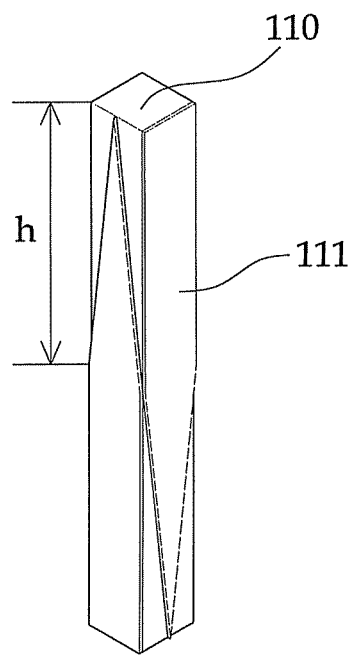
FIG. 3 is a perspective view showing a state in which the reflective film of the first embodiment is attached to the surface of a single crystal.

FIG. 3 is a perspective view showing a state in which the triangular tooth film 111 is attached to a single rectangular parallelepiped crystal 110. The crystal functions to absorb gamma rays having 511-keV energy and to emit scintillation light, and so it is called a scintillation light crystal. The crystal is used to detect the gamma rays and detect a position where the scintillation light is generated using the dispersion of light.

Meanwhile, the crystal according to the present embodiment is the rectangular parallelepiped crystal 110 having a square face. The rectangular parallelepiped crystal 110 has a section of 1.5 mm in width and 1.5 mm in height and has a length of 20 mm. The rectangular parallelepiped crystal 110 is of a Lutetium Oxyorthosilicate (LSO) rectangular parallelepiped crystal having the section unpolished and a refractive index of 1.82.

Figure 4:
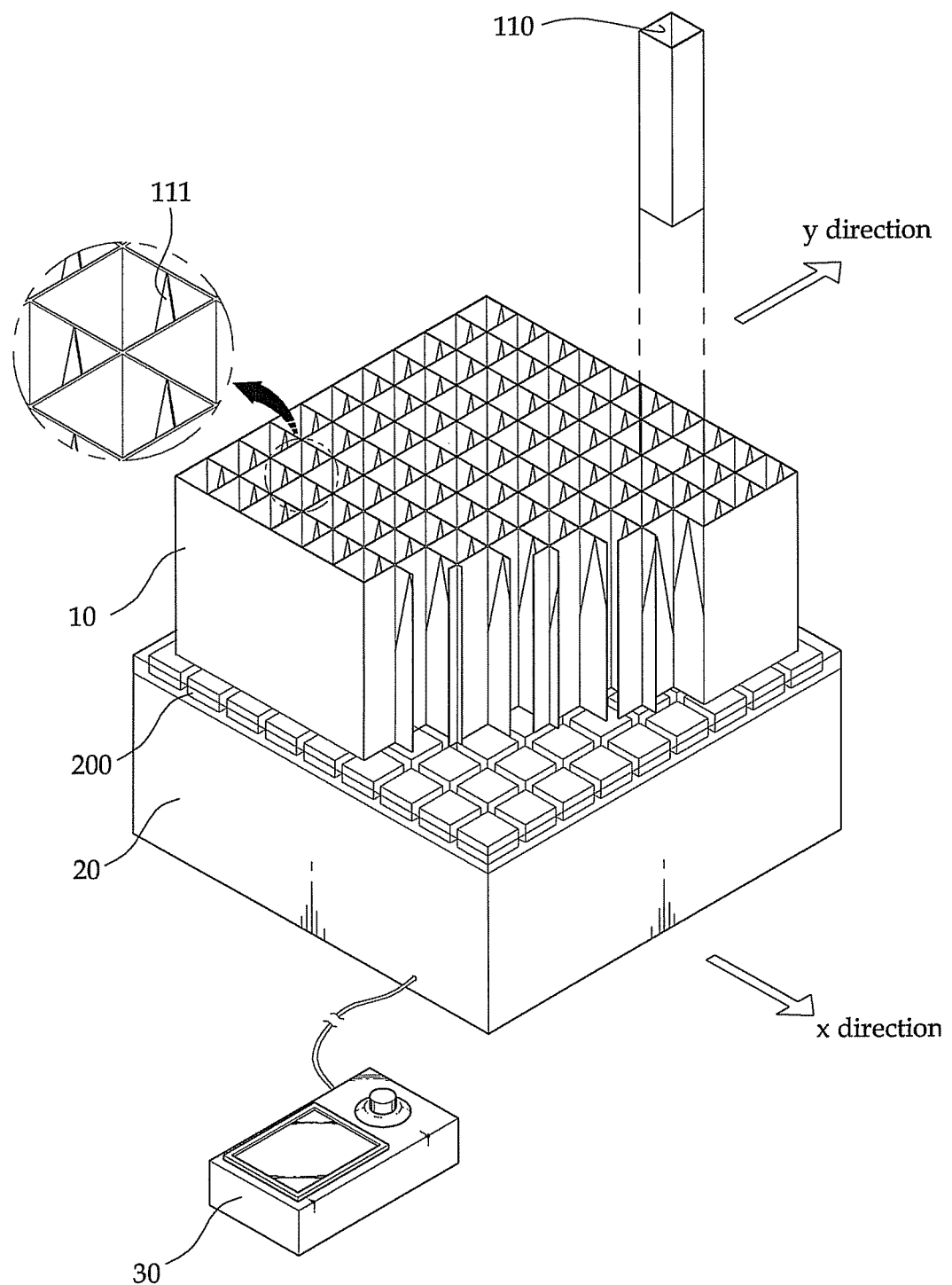
FIG. 4 is a perspective view showing the entire construction according to the first embodiment.

FIG. 4 is a perspective view showing the entire construction according to the first embodiment. The first embodiment includes the rectangular parallelepiped crystals 110, a crystal layer 10, the triangular tooth films 111, a position-sensitive PMT 20, and a control unit 30.

As shown in FIG. 4, the rectangular parallelepiped crystals 110 form an array of a square, thus constituting the crystal layer 10. The triangular tooth films 111 are attached between the rectangular parallelepiped crystals 110. Furthermore, the crystal layer 10 is connected to the position-sensitive PMT 20, and the position-sensitive PMT 20 is connected to the control unit 30.

The first embodiment relates to the construction in which the spread of scintillation light is controlled by changing the area of the reflective films attached to the x axis and the y axis on the basis of a DOI. Thus, the position-sensitive PMT 20 detects a different photon distribution according to a direction.

In the crystal layer 10, the same kind of the rectangular parallelepiped crystals 110 are arranged in a square of 29 rows×29 columns, and the lateral edges of the crystal layer 10 is optically shielded from a neighboring crystal layer by a reflective film.

The position-sensitive PMT (PS-PMT) 20 is one of scintillation light detectors, and it has a multi-anode array. One or more light-sensitive pixels 200 are formed on a portion of the position-sensitive PMT 20, which is connected to the crystal layer 10. Furthermore, the scintillation light detector can include a photosensor using a solid-state element other than the position-sensitive PMT 20.

In the construction of the present embodiment, the light-sensitive pixels 200 within the position-sensitive PMT 20 connected to the crystal layer 10 are arranged to have the square structure of 16 rows×16 columns. Furthermore, as shown in FIG. 4, since the DOI is measured by analyzing a 2-dimensional scintillation light signal according to each of the x axis and the y axis, the crystals within the light-sensitive pixels 200 and the crystal layer 10 need not to be matched in a one-to-one manner.

The control unit 30 is connected to the position-sensitive PMT 20 and configured to receive output signals, output from the x axis and the y axis of the crystal layer 10, from the position-sensitive PMT 20 and to calculate the DOI based on the received output signals.

Furthermore, the triangular tooth films 111 and the rectangular parallelepiped crystals 110, and the rectangular parallelepiped crystals 110 and the position-sensitive PMT 20 are bonded together using an optical cement or grease (i.e., an optical adhesive). The optical adhesive has a refractive index of 1.5.

<Second Embodiment>

The second embodiment relates to a construction in which the reflective film of the first embodiment is composed of only a gradient film 112. Only the differences between the first embodiment and the second embodiment are described below, for simplicity.

Figure 5:
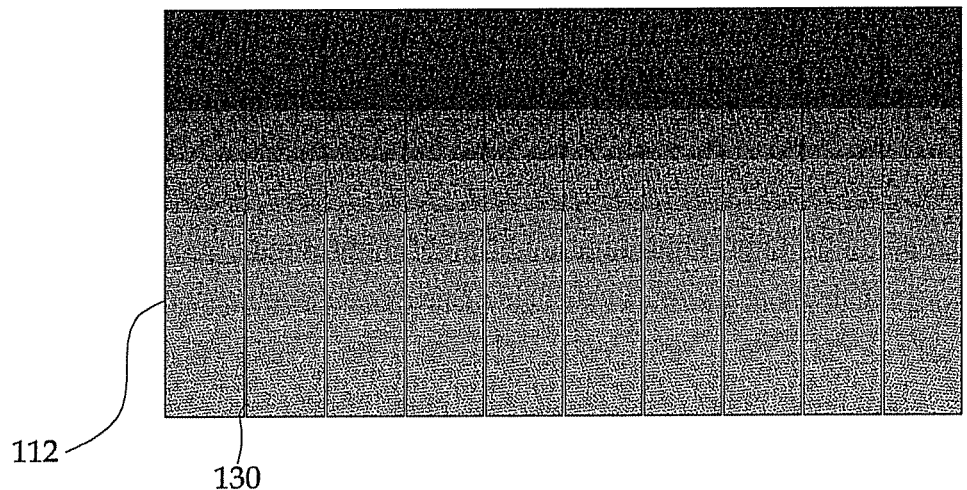
FIG. 5 is a front view of a reflective film according to a second embodiment.

As shown in FIG. 5, the reflective film is a rectangular strip having a rectangular shape. The reflective film is composed of the gradient film 112 in which a coupling groove 130 is formed every width on one side of a rectangular parallelepiped crystals 110 attached thereto and a concentration is linearly changed in the depth direction of the rectangular parallelepiped crystals 110.

Here, the gradient film 112 is formed by coating transparent vinyl, having the same thickness as that of the first embodiment, with white or silver paint (i.e., reflective materials). The gradient film 112 is formed to have reflectivity from the highest concentration to the fully transparent concentration so that the degree of light and shade can be gradually contrasted.

Furthermore, the gradient films 112 have a lattice structure in which they are arranged in parallel to one faces of the rectangular parallelepiped crystals 110 and consecutively arranged in the same manner so that the top surfaces of the gradient films 112 become transparent portions and the other faces at a right angle to the one faces of the rectangular parallelepiped crystals 110 are consecutively inserted in a reverse phase so that they can be coupled with the coupling grooves 130.

Figure 6:
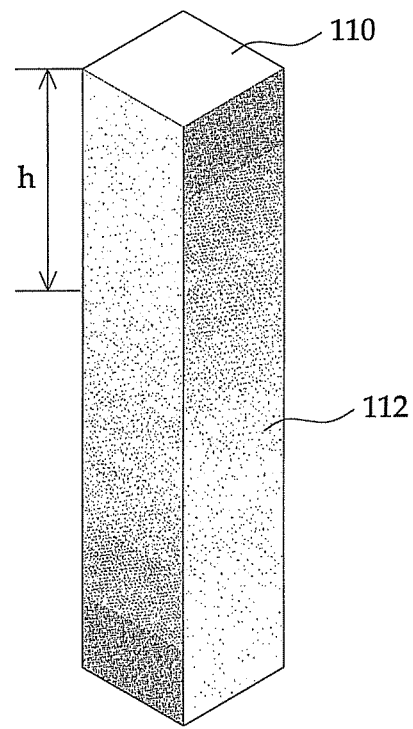
FIG. 6 is a perspective view showing a state in which the reflective film of the second embodiment is attached to the surface of a single crystal.

FIG. 6 is a perspective view showing a state in which the gradient film 112 is attached to a single rectangular parallelepiped crystal 110. The type, size, and refractive index of the rectangular parallelepiped crystal 110 are the same as those of the first embodiment. An optical adhesive used to couple the rectangular parallelepiped crystals 110 and the gradient films 112 together is the same as that of the first embodiment.

Figure 7:
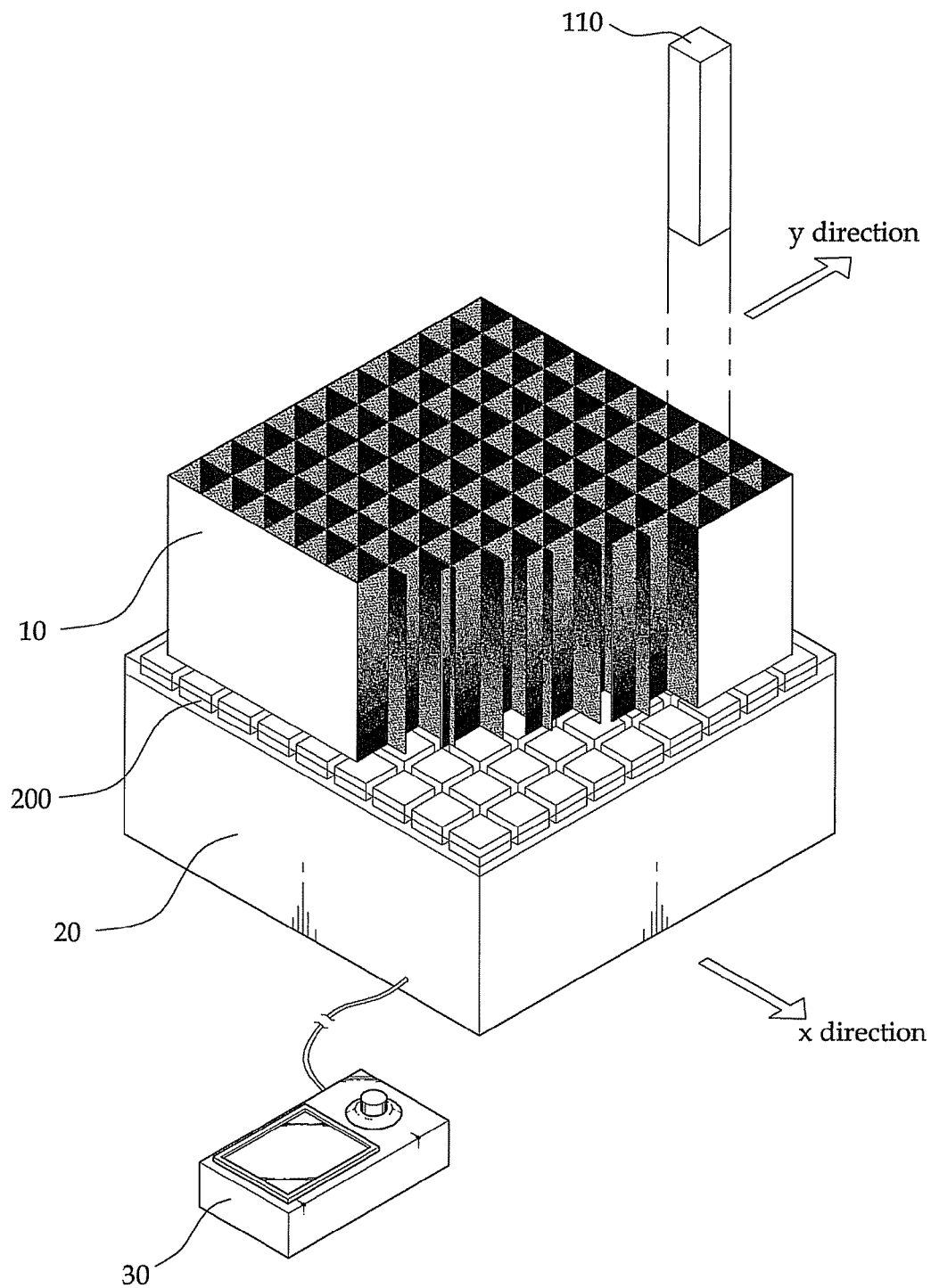
FIG. 7 is a perspective view showing the entire construction according to the second embodiment.

FIG. 7 is a perspective view showing the entire construction according to the second embodiment. The construction of the rectangular parallelepiped crystals 110, a crystal layer 10 of a mono layer, a position-sensitive PMT 20, and a control unit 30 and a coupling thereof are the same as those of the first embodiment except the gradient film 112 of the second embodiment.

The second embodiment is different from the first embodiment in that the spread of scintillation light is controlled by changing the concentration of the reflective films attached in the x axis and the y axis according to a DOI, but is identical with the first embodiment in that the position-sensitive PMT 20 detects the number of photons in each direction.

Furthermore, the type and refractive index of an optical adhesive used to couple the rectangular parallelepiped crystals 110 and the position-sensitive PMT 20 together are also the same as those of the first embodiment.

<Third Embodiment>

The third embodiment is the same as the first embodiment other than the constructions of crystals and reflective films. Accordingly, only the differences between the first embodiment and the third embodiment are described below, for simplicity.

Figure 8A:
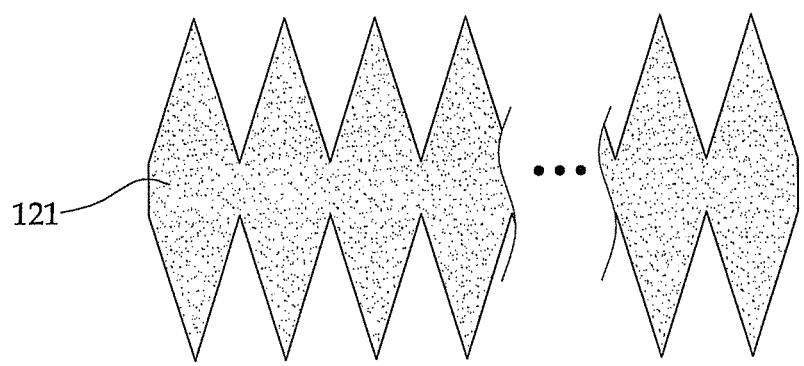
FIG. 8a is a front view of a diamond-shaped film in the reflective film of the third embodiment.
Figure 8B:
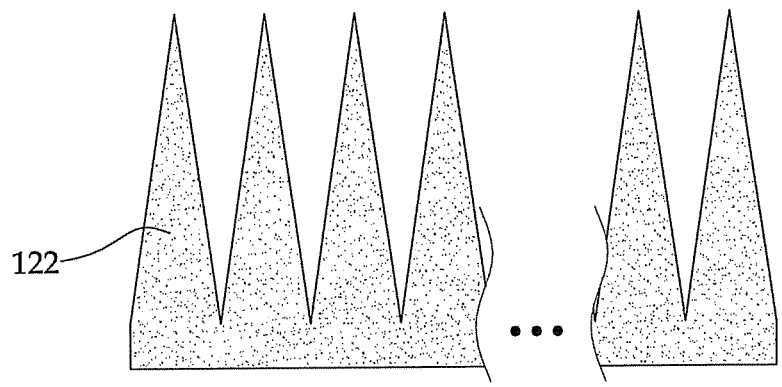
FIG. 8b is a front view of a triangular film in the reflective film of the third embodiment.
Figure 8C:
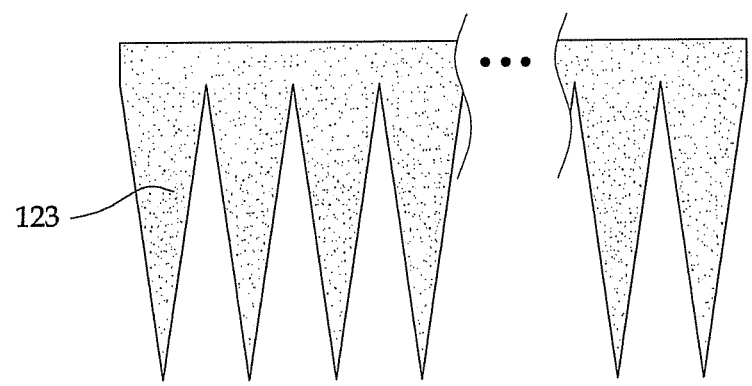
FIG. 8c is a front view of an inverse triangular film in the reflective film of the third embodiment.

FIG. 8*a* is a front view of a diamond-shaped film 121 having a single form of a diamond shape in the reflective film of the third embodiment. FIG. 8*b* is a front view of a triangular film 122 having a single form of a triangular shape in the reflective film of the third embodiment. FIG. 8*c* is a front view of an inverse triangular film 123 in the reflective film of the third embodiment. Here, the materials, reflectivity, and thickness of the film are the same as those of the first embodiment.

Furthermore, a shape in which the diamond-shaped film 121, the triangular film 122, or the inverse triangular film 123 is repeated for every lateral width of crystals attached thereto.

Figure 9A:
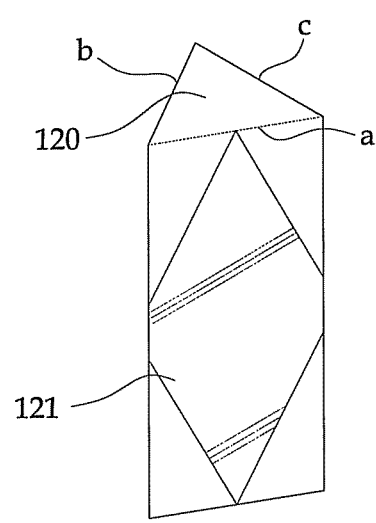
FIG. 9a is a perspective view showing a state in which the diamond-shaped film of the third embodiment is attached to the surface of a single crystal.
Figure 9B:
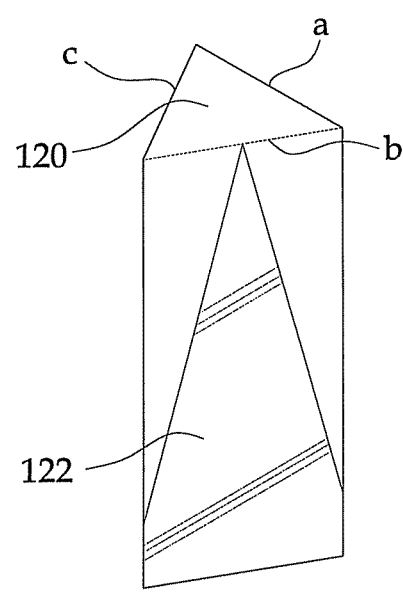
FIG. 9b is a perspective view showing a state in which the triangular film of the third embodiment is attached to the surface of a single crystal.
Figure 9C:
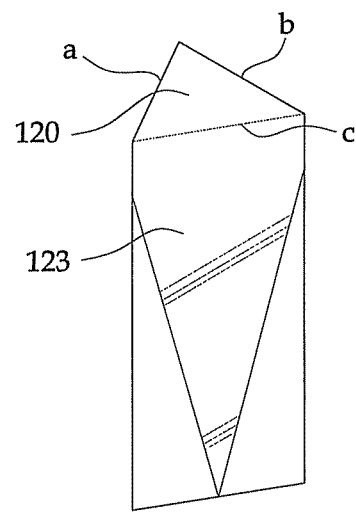
FIG. 9c is a perspective view showing a state in which the inverse triangular film of the third embodiment is attached to the surface of a single crystal

FIG. 9*a* is a perspective view showing a state in which the diamond-shaped film 121 of the third embodiment is attached to the surface of a single crystal. FIG. 9*b* is a perspective view showing a state in which the triangular film 122 of the third embodiment is attached to the surface of a single crystal. FIG. 9*c* is a perspective view showing a state in which the inverse triangular film 123 of the third embodiment is attached to the surface of a single crystal.

FIGS. 9*a*, 9*b*, and 9*c* are perspective views showing a state in which the reflective film is coupled to a single triangle pole-shaped crystal 120, seen from three directions (faces a, b, and c). The diamond-shaped film 121 is attached to the face a of the triangle pole-shaped crystal 120 as shown in FIG. 9*a*, the triangular film 122 is attached to the face b of the triangle pole-shaped crystal 120 as shown in FIG. 9*b*, and the inverse triangular film 123 is attached to the face c of the triangle pole-shaped crystal 120 as shown in FIG. 9*c*.

The crystal is the triangle pole-shaped crystal 120 having a section of a regular triangle shape. The type of the crystal is the same as that of the first embodiment, and an adhesive used to couple the crystals and the films together is also the same as that of the first embodiment.

Figure 10:
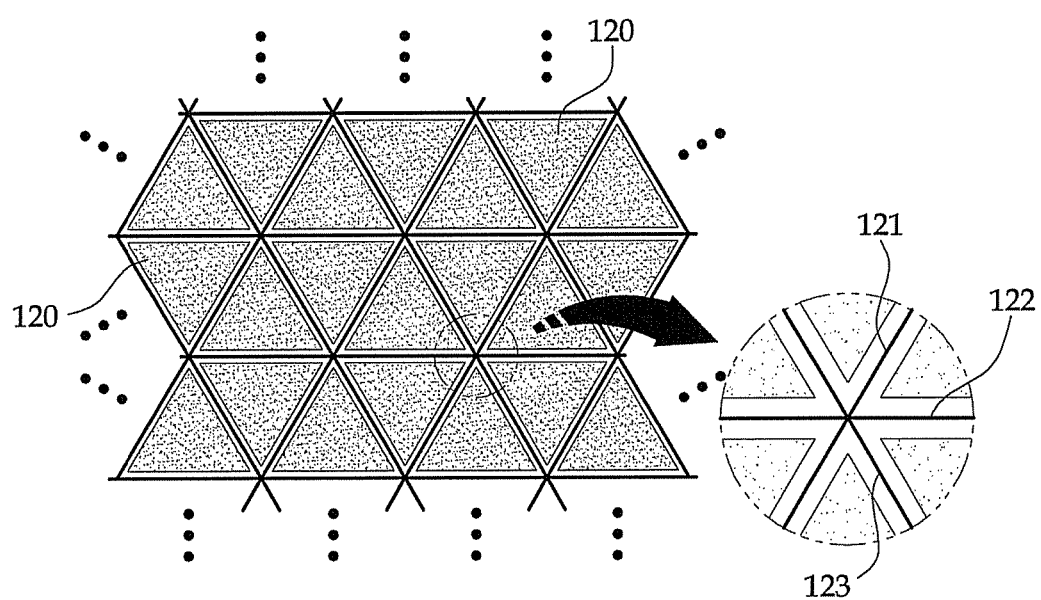
FIG. 10 is a partial plan view of a crystal layer composed of the crystals and the reflective films according to the third embodiment.

FIG. 10 is a partial plan view of a crystal layer composed of the crystals and the reflective films according to the third embodiment. The third embodiment is the same as the first embodiment in that the crystal layer of a mono layer, a position-sensitive PMT 20, and a control unit 30 are included except the crystals and the reflective films. Furthermore, a construction in which the crystal layers of a mono layer, comprising the triangle pole-shaped crystals 120, are coupled with the position-sensitive PMT 20 and an optical adhesive used for the combination are also the same as those of the first embodiment.

In the combination of the reflective films, as shown in FIGS. 9 and 10, the diamond-shaped films 121 are consecutively inserted and arranged in parallel to the one faces (i.e., the face a) of the respective triangle pole-shaped crystals 120, the triangular films 122 are consecutively inserted and arranged in parallel to the other faces (i.e., the face b) of the respective triangle pole-shaped crystals 120, and the inverse triangular film 123 are consecutively inserted and arranged in parallel to the remaining one faces (i.e., the face c) of the respective triangle pole-shaped crystals 120, thus forming a lattice structure.

The third embodiment has the same construction as the first and second embodiments in that the spread of scintillation light according to the direction is changed by preventing or permitting the spread of the scintillation light according to a DOI, but differs from the first and second embodiments in that it improves the resolution of a DOI by subdividing the direction. Accordingly, the third embodiment is the same as the second and third embodiments in that the position-sensitive PMT 20 detects a different photon distribution for every direction.

<Measurement Method>
<First Embodiment>

A method of measuring a DOI according to the first embodiment is described below. The method is described below with reference to FIG. 4.

The reflective films are inserted into and attached to the rectangular parallelepiped crystals 110. Here, one direction is assumed to be an x axis, and the triangular tooth films 111 oriented toward the upper part are attached to the rectangular parallelepiped crystals 110. The other direction at a right angle to the one direction is assumed to be a y axis, and the triangular tooth films 111 oriented toward the lower part are attached to the rectangular parallelepiped crystals 110.

Scintillation light generated at a position having a shallow DOI (that is, from an upper portion distant from the position-sensitive PMT 20) is spread only in the y-axis direction, and so the number of photons detected in the x-axis direction will be small. Accordingly, the method of measuring an unknown DOI in accordance with such a principle is performed as follows.

Figure 11:
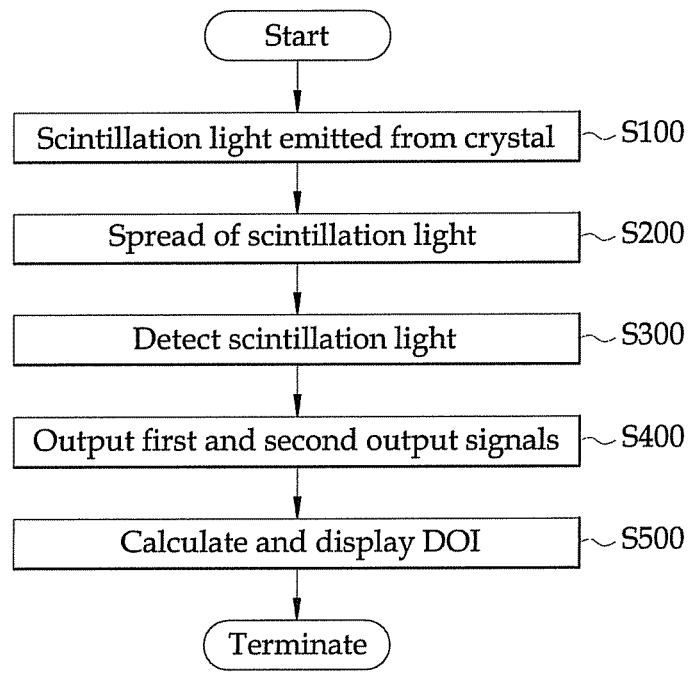
FIG. 11 is an overall flowchart illustrating a method of measuring a DOI.

FIG. 11 is a flowchart illustrating the method of measuring a DOI. Referring to FIG. 11, first, scintillation light is emitted from a specific position of the rectangular parallelepiped crystal 110 which has absorbed gamma rays at step S100. The degree of dispersion of the scintillation light is changed by the triangular tooth film 111 which area is changed in the length direction of the rectangular parallelepiped crystal 110 at step 5200.

The photons spread by the dispersion of the scintillation light are detected by the position-sensitive PMT disposed at one end of the rectangular parallelepiped crystals 110 at step 5300. The position-sensitive PMT 20 outputs a first output signal, corresponding to the number of photons of the scintillation light, and a second output signal according to a direction at a right angle to the one direction at step S400.

Next, the control unit 30 receives the first and second output signals according to each 2-dimensional direction for every channel, calculates a DOI of the rectangular parallelepiped crystal 110, and displays the calculation results on a display unit at step S500.

Figure 12:
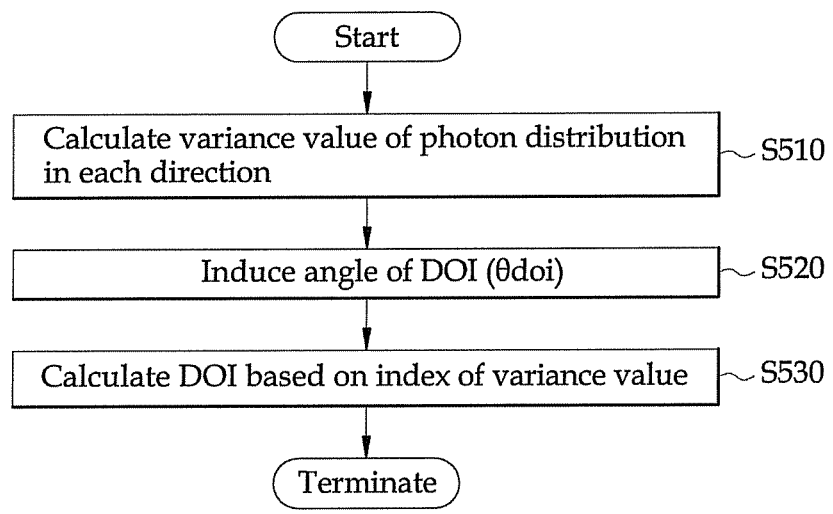
FIG. 12 is a flowchart illustrating a method of calculating a DOI.

The method of calculating the DOI is described below in detail with reference to FIG. 12.

First, the control unit 30 calculates a variance value of the number of photons in each direction on the basis of the first and second output signals as follows at step S510.

$$\sigma_x^2 = \frac{\sum_i (x_i^2 - x_0^2) \times N_{xi}}{\sum_i N_{xi}},$$ [Equation 1]

$$\sigma_y^2 = \frac{\sum_i (y_i^2 - y_0^2) \times N_{yi}}{\sum_i N_{yi}},$$ [Equation 2]

Here, $x_i$ and $y_i$ indicate respective $i^{th}$ positions of x and y in the light-sensitive pixel. Furthermore, $N_{xi}$ indicates the sum of counted photons of $i^{th}$ light-sensitive pixels in the x axis, and $N_{yi}$ indicates the sum of counted photons of $i^{th}$ light-sensitive pixels in the y axis. Furthermore, $x_0$ indicates the mean of $x_i$ for $N_{xi}$, and $y_o$ indicates the mean of $y_i$ for $N_{yi}$.

A DOI angle ($\theta_{doi}$) is defined on the basis of the variance value, and a DOI is calculated on the basis of the DOI angle.

Figure 13:
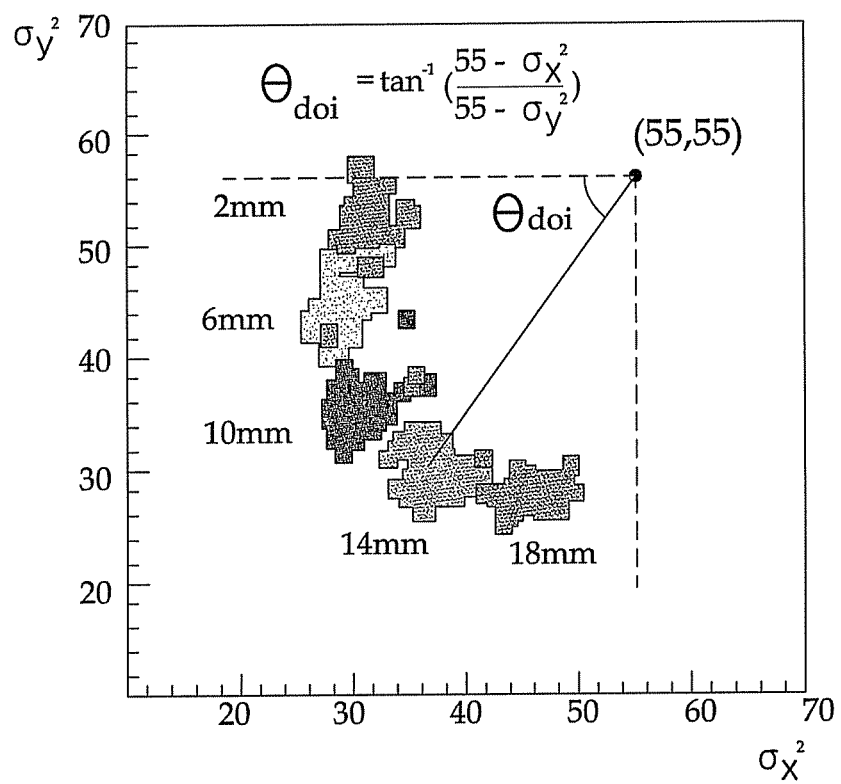
FIG. 13 is a graph showing variance values in the directions according to DOIs within the crystals (positions spaced apart from a position-sensitive PMT by 2 mm, 6 mm, 10 mm, 14 mm, and 18 mm)

FIG. 13 is a graph showing variance values of photon distributions detected by position-sensitive PMT. Squares indicate distributions in the x and y directions resulting from single scintillation light. As shown in FIG. 13, the variance values of respective directions according to DOIs (2 mm, 6 mm, mm, 14 mm, and 18 mm are distances from the position-sensitive PMT) are measured within the rectangular parallelepiped crystal 110, and indices on the coordinate plane are found. The graph of FIG. 13 generally has a quadrant shape. Furthermore, in the graph of FIG. 13, an angle formed by a line, connecting the center (experiment example: 55,55) of the quadrant in a radius direction and a 2-dimensional variance value coordinate point, and the x dispersion axis is defined as the DOI angle ($\theta_{doi}$).

Furthermore, as shown in FIG. 13, the DOI angle ($\theta_{doi}$) can be found using the following equation induced in accordance with the geometrical principle on the coordinate plane at step S520.

$$\theta_{doi} = \tan^{-1}\left(\frac{55 - \sigma_y^2}{55 - \sigma_x^2}\right)$$ [Equation 3]

The DOI angle ($\theta_{doi}$) found using the above equation corresponds to an index value from which a position according to the DOI can be known. Furthermore, consecutive DOI information can also be known on the basis of the index value at step S530.

Figure 14:
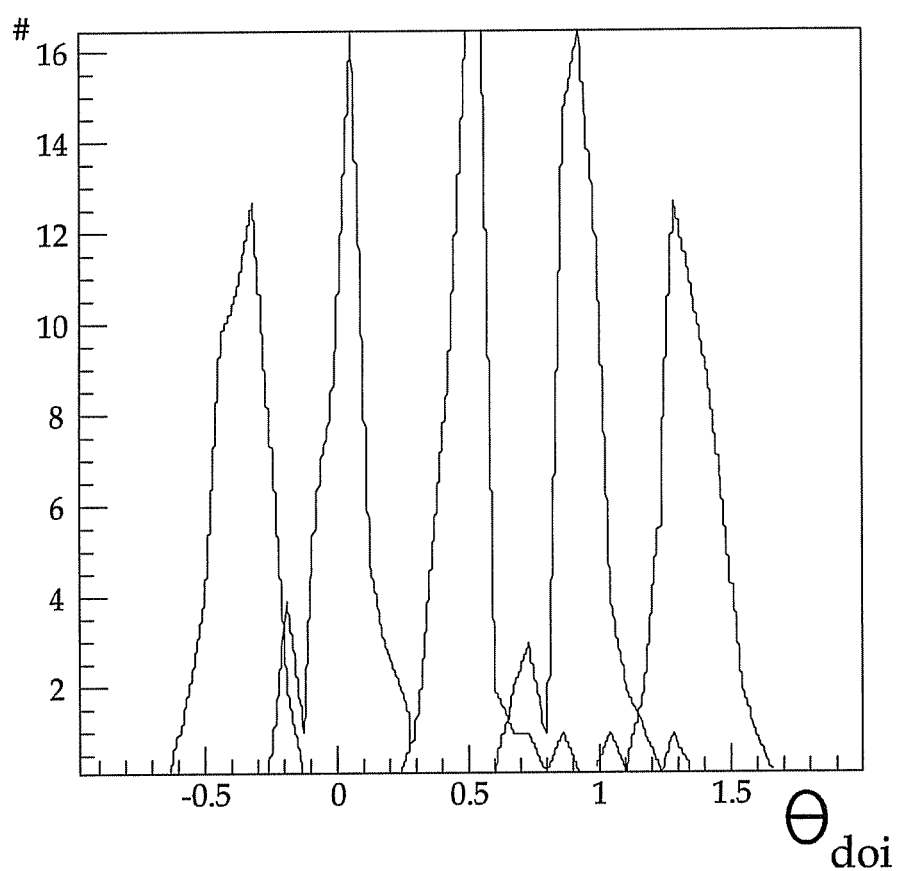
FIG. 14 is a histogram showing DOI variance values according to DOI angles ($\theta_i$).

FIG. 14 is a histogram showing the DOI variance values of DOIs (2 mm, 6 mm, 10 mm, 14 mm, and 18 mm are distances from the position-sensitive PMT) according to $\theta_{doi}$ (or radian values). The x axis indicates $\theta_{doi}$ (or radian values), and the y axis indicates the number of variance values. A DOI resolution shown in FIG. 14 is a value calculated from full width at half maximum (FWHM) between peaks and is the average of 1.7 mm.

<Second Embodiment>

A method of measuring a DOI according to the second embodiment is described below. The method is described with reference to FIG. 7. The reflective films are inserted into and attached to the rectangular parallelepiped crystals 110.

One direction is assumed to be an x axis, and the gradient films 112 having a transparent top surface are attached to the rectangular parallelepiped crystals 110. The other direction at a right angle to the one direction is assumed to be a y axis, and the gradient films 112 having a transparent bottom surface are attached to the rectangular parallelepiped crystals 110.

Scintillation light generated at a position having a shallow DOI (that is, from an upper portion distant from the position-sensitive PMT 20) is spread only in the y-axis direction, and so the number of photons detected in the x-axis direction will be small. To the contrary, scintillation light generated at a position having a deep DOI (that is, from a lower portion close to the position-sensitive PMT 20) is spread only in the x-axis direction, and so the number of photons detected in the x-axis direction will be small. Accordingly, the method of measuring an unknown DOI in accordance with the principle is the same as that of the first embodiment.

<Third Embodiment>

A method of measuring a DOI according to the third embodiment is described below. The method is described with reference to FIG. 10. The reflective films are inserted into and attached to the triangle pole-shaped crystal 120, and an angle formed by the reflective films is 60°.

When scintillation light is generated, a large number of photons are detected at positions having a shallow DOI along the diamond-shaped films 123, a large number of photons are detected at positions having a DOI half the length of the crystals along the triangular films 121, and a large number of photons are detected at positions having a deep DOI along the diamond-shaped films 123. Accordingly, the method of measuring an unknown DOI in accordance with the principle is the same as that of the first embodiment.

As described above, the present invention has an advantage in that it can improve and maintain the spatial resolution through the arrangement of the reflective films, while using the crystal layer of a mono layer, and statistical approaches, in acquiring DOI information for the improvement of the spatial resolution of PET equipment which was problematic in the prior art.

Furthermore, the present invention can obtain a better DOI resolution even using a PMT having a multi-channel because it estimates the DOI by measuring a tendency of 2-dimensional distributions of light dispersion.

Furthermore, the present invention provides consecutive DOI information by solving the discontinuity of DOI information in the existing model using a multi-crystal layer.

Furthermore, the present invention has an advantage in that the number of light pixels of a photosensor as many as the number of crystals is not required because the crystals and the pixels of the photosensor need not to be individually matched. Further, the present invention has an advantage in that the costs can be reduced and the assembly is easy because the size of the crystal is not limited.

Furthermore, the present invention has an advantage in that the costs can be reduced because additional photosensors and electronic equipment need not to be added as compared with the existing model using the photosensors on both sides of crystals.

Furthermore, the present invention is practical because the method and apparatus for measuring a DOI using the dispersion of light can be applied to not only a positron tomography apparatus, but also a SPECT, a CT, a Compton camera, and a gamma camera using radioactive rays.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. An apparatus for measuring a Depth-Of-Interaction (DOI) using a light dispersion, the apparatus comprising:
    a crystal layer of a mono layer in which a plurality of crystals for absorbing gamma rays are adjacent and consecutively arranged;
    scintillation light detectors disposed at one end of the crystals and configured to detect scintillation light emitted from the crystal layer by the gamma rays;
    a change material included in the crystals and configured to linearly change transmittance in a length direction of the crystals; and
    a control unit configured to calculate the DOI in the crystal layer on a basis of a first output signal and a second output signal;
    the scintillation light detectors outputting the first output signal in one direction and the second output signal in a direction perpendicular to the one direction;
    said control unit configured to calculate the DOI of the crystal layer by at least
        calculating an amount of a variance value of photon distribution in each of the directions on the basis of the first output signal and the second output signal,
        inducing an angle of the DOI on the basis of the variance value of the number of photons, and
        calculating the DOI on the basis of the angle of the DOI.

2. The apparatus as in claim 1 wherein the change material is based on a coating concentration of reflective materials in the length direction of the crystals.

3. The apparatus as in claim 2 wherein the reflective materials include white or silver paint.

4. The apparatus as in claim 1 wherein the change material comprises a reflective film inserted between the crystals.

5. The apparatus as in claim 4 wherein the reflective film is based on a geometric change of the reflective film in the length direction of the crystals.

6. The apparatus as in claim 5 wherein the reflective film is a triangular tooth film having a long strip and a triangular shape in which a width of the crystal is a base and half a length of the crystal is a height on one face of the length direction, wherein the triangular shapes are repeatedly formed every width of the crystal.

7. The apparatus as in claim 6 wherein the crystal is a rectangular parallelepiped crystal having a square cross-section; and wherein the triangular tooth films are consecutively arranged in parallel to one side of the rectangular parallelepiped crystals and inserted into the rectangular parallelepiped crystals in a reverse phase on sides vertical to the one sides.

8. The apparatus as in claim 7 wherein the rectangular parallelepiped crystal has a refractive index of 1.82 on an unpolished surface; and wherein the crystal layer has a square in which an arrangement of the rectangular parallelepiped crystals is 29 rows×29 columns.

9. The apparatus as in claim 8 wherein the rectangular parallelepiped crystal has a square cross-section having one face of 1.5 mm and having a length of 12 mm to 24 mm.

10. The apparatus as in claim 5 wherein the reflective film is a film of a strip shape in which identical shapes are repeated for every width of one side of the crystal in one face of the length direction and is a diamond-shaped film having a single form of a diamond shape or a triangular film having a single form of a triangular shape.

11. The apparatus as in claim 10 wherein the crystal is a triangle pole-shaped crystal having a regular triangle cross-section; wherein the diamond-shaped films are consecutively arranged in parallel to one sides of the triangle pole-shaped crystals; wherein the triangular films are consecutively arranged in parallel on the other sides of the triangle pole-shaped crystals crossing the one face; and wherein inverse triangular films are consecutively arranged in a reverse phase of the triangular film on remaining sides of the triangle pole-shaped crystals.

12. The apparatus as in claim 4 wherein the reflective film is based on a change in a concentration of the reflective film in a length direction of the crystals.

13. The apparatus as in claim 12 wherein the reflective film is a gradient film having a rectangular strip of a rectangular shape, a coupling groove formed for every width on one sides of the crystals, and a linear change in the concentration in the length direction of the crystals.

14. The apparatus as in claim 13 wherein the gradient film is formed by coating white or silver paint on transparent vinyl.

15. The apparatus as in claim 13 wherein the crystal is a rectangular parallelepiped crystal having a square face; and wherein the gradient films are consecutively inserted into and arranged on the rectangular parallelepiped crystals in parallel to one side of the rectangular parallelepiped crystals so that a top surface of the gradient films becomes a transparent portion and are consecutively inserted into and arranged on the rectangular parallelepiped crystals in a reverse phase of the gradient film on the other sides of the rectangular parallelepiped crystals, vertical to the one face, so that the gradient films can be coupled with the coupling grooves.

16. The apparatus as in claim 1 wherein the crystal is any one of LSO, BGO, and NaI crystals.

17. The apparatus as in claim 1 wherein the scintillation light detector comprises a position-sensitive Photo Multiplier Tube (PMT) equipped with one or more light-sensitive pixels.

18. The apparatus as in claim 17 wherein the position-sensitive Photo Multiplier Tube (PMT) has a structure in which the light-sensitive pixels coupled with the crystal layer are arranged to have a square structure of 16 rows×6 columns or 8 rows×8 columns.

19. A Positron Emission Tomography (PET) device using light dispersion comprising:
    a device for measuring a Depth-Of-Interaction (DOI) using the light dispersion, the device comprising
        a crystal layer of a mono layer in which a plurality of crystals for absorbing gamma rays are adjacent and consecutively arranged,
        scintillation light detectors disposed at one end of the crystals and configured to detect scintillation light emitted from the crystal layer by the gamma rays,
        a change material included in the crystals and configured to linearly change transmittance in a length direction of the crystals, and
        a control unit configured to calculate the DOI in the crystal layer on a basis of a first output signal and the second output signal,
        the scintillation light detectors outputting the first output signal in one direction and the second output signal in a direction perpendicular to the one direction,
        said control unit configured to calculate the DOI of the crystal layer by at least
            calculating an amount of a variance value of photon distribution in each of the directions on the basis of the first output signal and the second output signal,
            inducing an angle of the DOI on the basis of the variance value of the number of photons, and
            calculating the DOI on the basis of the angle of the DOI.

20. A method of measuring a Depth-Of-Interaction (DOI) using light dispersion, the method comprising:
    emitting scintillation light from specific positions of a plurality of crystals, which have absorbed gamma rays;
    the crystals or reflective films having a linearly changing transmittance in a length direction of the crystals and controlling a degree of dispersion of scintillation light;
    using scintillation light detectors, disposed on one end of the crystals, to detect the scintillation light;
    using the scintillation light detectors, each detecting first output signal according to one direction corresponding to the scintillation light and a second output signal according to a direction at a right angle to the one direction; and
    using a control unit to calculate the DOI of the crystal on a basis of the first output signal and the second output signal by at least
        calculating an amount of a variance value of photon distribution in each of the directions on the basis of the first output signal and the second output signal,
        inducing an angle of the DOI on the basis of the variance value of the number of photons, and
        calculating the DOI on the basis of the angle of the DOI.

21. The method as in claim 20 wherein the DOI angle is calculated using a following equation:

$$\theta_{doi} = \tan^{-1}\left(\frac{55 - \sigma_y^2}{55 - \sigma_x^2}\right)$$

where $\theta_{doi}$ is an angle of the DOI, $\sigma_x^2$ is a variance value in an x axis, and $\sigma_y^2$ is a variance value in an y axis.

* * * * *